(12) United States Patent
Hennet et al.

(10) Patent No.: US 11,026,959 B2
(45) Date of Patent: *Jun. 8, 2021

(54) SYNTHETIC COMPOSITION AND METHOD FOR TREATING IRRITABLE BOWEL SYNDROME

(71) Applicant: Glycom A/S, Hørsholm (DK)

(72) Inventors: Thierry Hennet, Otelfingen (CH); Bruce McConnell, La Tour de Peilz (CH); Emma Elison, Hjärup (SE); Louise Kristine Vigsnæs, København NV (DK)

(73) Assignee: Glycom A/S, Hørsholm (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/897,099

(22) Filed: Feb. 14, 2018

(65) Prior Publication Data

US 2018/0169122 A1    Jun. 21, 2018

Related U.S. Application Data

(63) Continuation of application No. 15/034,593, filed as application No. PCT/DK2015/050332 on Oct. 29, 2015, now abandoned.

(30) Foreign Application Priority Data

Oct. 29, 2014 (DK) .............. PA 2014 70663

(51) Int. Cl.
| | | |
|---|---|---|
| A61K 31/70 | (2006.01) | |
| A61K 31/7012 | (2006.01) | |
| A61K 31/7004 | (2006.01) | |
| A23L 33/21 | (2016.01) | |
| A61K 31/702 | (2006.01) | |
| A61P 1/04 | (2006.01) | |
| A23C 9/20 | (2006.01) | |

(52) U.S. Cl.
CPC ............ *A61K 31/702* (2013.01); *A23C 9/206* (2013.01); *A23L 33/21* (2016.08); *A61K 31/7004* (2013.01); *A61K 31/7012* (2013.01); *A61P 1/04* (2018.01); *A23V 2002/00* (2013.01)

(58) Field of Classification Search
CPC ............ A61K 31/7004; A61K 31/7012; A61K 31/702; A61K 2300/00
USPC ...................................... 514/23, 61
See application file for complete search history.

(56) References Cited

U.S. PATENT DOCUMENTS

| | | | |
|---|---|---|---|
| 4,663,321 A | 5/1987 | Bock et al. | |
| 2007/0185094 A1 | 8/2007 | Lattmann et al. | |
| 2012/0171165 A1* | 7/2012 | Buck ................ | A61K 31/702 514/23 |
| 2012/0171166 A1 | 7/2012 | Chow et al. | |
| 2012/0172319 A1 | 7/2012 | Chow et al. | |
| 2013/0195803 A1 | 8/2013 | German et al. | |
| 2013/0251844 A1 | 9/2013 | Sprenger | |
| 2013/0315990 A1* | 11/2013 | Bode ................... | A61K 35/741 424/451 |
| 2014/0249103 A1 | 9/2014 | Buck et al. | |
| 2018/0177809 A1 | 6/2018 | McConnell et al. | |
| 2018/0185398 A1 | 7/2018 | Vigsnaes et al. | |

FOREIGN PATENT DOCUMENTS

| | | |
|---|---|---|
| WO | 0104341 | 1/2001 |
| WO | 2004026257 | 4/2004 |
| WO | 2007101862 | 9/2007 |
| WO | 2009131537 | 10/2009 |
| WO | 2010115934 | 10/2010 |
| WO | 2010115935 | 10/2010 |
| WO | 2011005681 | 1/2011 |
| WO | 2011005681 A1 | 1/2011 |
| WO | 2011100979 | 8/2011 |
| WO | 2011100980 | 8/2011 |
| WO | 2012007588 | 1/2012 |
| WO | 2012009315 | 1/2012 |
| WO | 2012092160 | 7/2012 |
| WO | 2012/106665 A2 | 8/2012 |
| WO | 2012106665 A2 | 8/2012 |
| WO | 2012113404 | 8/2012 |
| WO | 2012113405 | 8/2012 |
| WO | 2012127410 | 9/2012 |
| WO | 2012155916 | 11/2012 |
| WO | 2012156897 | 11/2012 |
| WO | 2012156898 | 11/2012 |
| WO | 2013044928 | 4/2013 |
| WO | 2013091660 | 6/2013 |
| WO | 2013139344 | 9/2013 |
| WO | 2013148134 | 10/2013 |
| WO | 2013154725 | 10/2013 |
| WO | 2013154725 A1 | 10/2013 |
| WO | 2015077233 | 5/2015 |
| WO | 2015157098 | 10/2015 |

OTHER PUBLICATIONS

Camilleri, M. N. Engl. J. Med., 2012, 367(17), 1626-35.*
Gavini et al, Microbial Ecology in Health and Disease, 2001, 13, 40-45.*
U.S. Appl. No. 15/034,593, Office Action Summary, dated Nov. 14, 2017.
Chaturvedi, P., "Milk Oligosaccharide profiles by reversed-phase HPLC of their perbenzoylated derivatives", Analytical Biochemistry, vol. 251, pp. 89-97; whole document doi:10.1006/abio.1997.2250, (Sep. 1997).
O'Mahony, L. et al., "Lactobacillus and bifidobacterium in irritable bowel syndrome: symptom responses and relationship to cytokine profiles", Gastroenterology, 128:3:541-551: whole document, (Mar. 2005).

(Continued)

*Primary Examiner* — Ganapathy Krishnan
(74) *Attorney, Agent, or Firm* — Kunzler Bean & Adamson

(57) ABSTRACT

The application relates to a method for treating a patient with irritable bowel syndrome (IBS), the method comprising administering to the patient a mixture comprising 2'-fucosyllactose (2'-FL) and lacto-N-neotetraose (LNnT).

20 Claims, No Drawings

(56) References Cited

OTHER PUBLICATIONS

Silk, D. et al., "Clinical trial: the effects of a trans-galactooligosaccharide prebiotic on faecal microbiota and symptoms in irritable bowel syndrome", Alimentary Pharmacology & Therapeutics, doi:10.1111/j.1365-2036.2008.03911.x, (Nov. 28, 2008).

Walker M. et al., "Duodenal mastoctosis, eosinophilia and intaepithelial lymphocytosis ans possible disease markers in the irritable lowel syndrome and functional dyspepsia", Alimentary Pharmacology & Therapeutics, 29(7_765-773, doi:10.111/j.1365-2036.2009.03937.x, (Apr. 2009).

Buhner, S. et al., "Mast cell-nerve axis with a focus on the human gut", Biochimica et Biophysica Acta, 1822, pp. 85-92, doi:10.1016/j.bbadis.2001.06.004, (2012).

Sikandar, S. et al., "Visceral pain-the ins and Outs, the Ups and Downs", Curr Opin Support Palliat Care, 6(1):17-26, doi:10.1097/SPC.0b013e32834f6ec9, (Mar. 2012).

Kim, G. et al., "Methanobrevibacter smithii is the predominant methanogen in patients with constipation-predominant IBM and methane on breath", Dig Dis Sci, vol. 57, pp. 3213-3218, doi:10.1007/s10620-012-2197-1, (2012).

Bassett, J. et al., "A review of irritable bowel syndrome and an update on therapeutic approaches", Informa Healthcare, Expert Opin. Pharmacother, 9(7):1129-1143, doi:10.1517/14656560802048902, (2008).

Longstreth, G. et al., "Functional bowel disorders", Gastrenterology, vol. 130, pp. 1480-1491, doi:10.1053/j.gastro.2005.11.061, (2006).

Spiller R. et al., "Postinfectious irritable bowel syndrome", Gastroenterology, vol. 136, pp. 1979-1988, doi:10.1053/j.gastro.2009.02.074, (2009).

Guilatre M., et al., "Diarrheoa-predominant IBS patients show mast cell activation and hyperplasia in the jejunum", Gut, vol. 56, pp. 203-209, doi:10.1136/gut.2006.100594, (2007).

Spiller, R. et al., "Guidelines on the irritable bowel syndrome: mechanisms and practical management", Gut, vol. 56, pp. 1770-1798, doi:10.1136/gut.2007.119446, (2007).

Staudacher, H. et al., "Comparision of symptom response following advice for a diet low in fermentable carbohydrates (FODMAPs) verus standard dietary advice in patients with irritable bowel syndrome", Journal of Human Nutrition and Dietetics, vol. 24, pp. 487-495 (2011).

Zhang, L. et al., "Mast cells and irritable bowl syndrome: from the bench to the bedside", Journal of Neurogastroenterology and Motility, 22:2:181-192, (Apr. 2016).

Shulman R. et al., "Increased gastrointestinal permeability and gut inflammation in children with functional abdominal pain and irritable bowel syndrome", J. Pediatr., 153(5):646-650, doi:10.1016/j.jpeds.2008.04.062, (Nov. 2008).

Ohman, L. et al., "Crosstalk at the mucosal border: importance of the gut microenvironment in IBS", Nat, Rev. Gastroenterol., vol. 12, pp. 36-49, doi:10.1038/nrgastro.2014.200, (Jan. 2015).

Qin, J. et al., "A human gut microbial gene catalogue established by metagenomic sequencing", Nature, vol. 464, pp. 59-67, doi:10.1038/nature08821, (Mar. 4, 2010).

Schoepfer, A. et al., "Antibodies to flagellin indicate reactivity to bacterial antigens in IBS patients", Neurogastroenterol Motil, vol. 20, pp. 1110-1118, doi:10.1111/j.1365-2982.2008.01166.x, (2008).

Kerckhoffs, A. et al., "Lower bifidobacteria counts in both duodenal mucosa-associated and fecal microbiota in irritable bowel syndrome patients", World J. Gastroenterol, 15(23):2887-2892, doi:10.3748/wjg.15.2887, (Jun. 21, 2009).

Urashima, T. et al., "Mild Oligosaccharides", Nutrition and Diet Resarch Progress, Nova Biomedical Books, New York, (2011).

Jeffery, I. et al., An irritable bowel syndrome subtype defined by species-specific alterations in faecal microbiota, GUT 2012, 61:997-1006, published on Dec. 16, 2011, doi:10.1136/gutjnl-2011-301501, pp. 997-1006.

Thapar et al., "Diarrhoea in children: an interface between developing and developed countries", The Lancet, vol. 363, Feb. 21, 2004, www.lancet.com, pp. 641-653.

U.S. Appl. No. 15/147,112, Office Action Summary, dated Apr. 21, 2017.

U.S. Appl. No. 15/147,115, Office Action Summary, dated Apr. 21, 2017.

U.S. Appl. No. 15/147,112, Office Action Summary, dated Nov. 24, 2017.

U.S. Appl. No. 15/147,115, Office Action Summary, dated Nov. 27, 2017.

U.S. Appl. No. 15/034,593, Office Action Summary, dated Apr. 20, 2017.

Michael Camilleri, "Peripheral Mechanisms in Irritable Bowel Syndrome", N Engl J. Med. 367;17, Oct. 25, 2012, NEJM.org, pp. 1626-1635.

European Patent Office, "Extended European Search Report", application 15854904.8, dated Jun. 12, 2018, pp. 1-7.

U.S. Appl. No. 15/903,959, Office Action Summary, dated May 14, 2019, pp. 1-39.

U.S. Appl. No. 15/906,911, Office Action Summary, dated May 14, 2019, pp. 1-38.

U.S. Appl. No. 16/706,627, "Office Action Summary", USPTO, dated May 29, 2020, pp. 1-26.

China PTO, "Notification of the First Office Action", dated Mar. 28, 2019, pp. 1-7.

Europe PTO, "Communication pursuant to Article 94(3) EPC", dated Dec. 12, 2019, pp. 1-3.

L. O'Mahony et al., "Lactobacillus and Bifidobacterium in Irritable Bowel Syndrome: Symptom Responses and Relationship to Cytokine Profiles", Gastroenterology 2005;128:pp. 541-551.

E. Elison et al., "Oral supplementation of healthy adults with 2!-O-fucosyllactose and lacto-N-neotetraose is well tolerated and shifts the intestinal microbiota", British Journal of Nutrition, Aug. 22, 2016, pp. 1-13.

G. Gibson et al., "The International Scientific Association for Probiotics and Prebiotics (ISAPP) consensus statement on the definition and scope of prebiotics", Nature Reviews | Gastroenterology & Hepatology, vol. 14, Aug. 2017, pp. 491-502.

U.S. Appl. No. 15/903,959, Final Office Action, dated Dec. 20, 2019, pp. 1-24.

U.S. Appl. No. 15/906,911, Final Office Action, dated Dec. 20, 2019, pp. 1-22.

D. Barile et al., "Human milk and related oligosaccharides as prebiotics", Biotechnology, Feb. 19, 2013, pp. 214-219.

M. Haarman et al., Quantitative Real-Time PCR Assays to Identify and Quantify Fecal Bifidobacterium Species in Infants Receiving a Prebiotic Infant Formula, Applied and Environmental Microbiology, vol. 71, No. 5, May 2005, pp. 2318-2324.

N. Sprenger et al., "Longitudinal change of selected human milk oligosaccharides and association to infants' growth, an observatory, single center, longitudinal cohort study", PLOS ONE, Feb. 9, 2017, pp. 1-15.

U.S. Appl. No. 15/903,959, Office Action Summary, dated Jul. 31, 2020, pp. 1-48.

U.S. Appl. No. 15/906,911, Office Action Summary, dated Jul. 24, 2020, pp. 1-34.

J. Yang, "Lactose intolerance in irritable bowel syndrome patients with diarrhoea: the roles of anxiety, activation of the innate mucosal immune system and visceral sensitivity", Alimentary Pharmacology and Therapeutics, 2014, 39, pp. 302-311.

\* cited by examiner

SYNTHETIC COMPOSITION AND METHOD FOR TREATING IRRITABLE BOWEL SYNDROME

CROSS-REFERENCES TO RELATED APPLICATIONS

This is a continuation application of and claims priority to U.S. patent application Ser. No. 15/034.593 entitled SYNTHETIC COMPOSITION AND METHOD FOR TREATING IRRITABLE BOWEL SYNDROME and filed on May 5, 2016 for Thierry Hennet et al., and claims the priority to PCT/DK2015/050332 entitled SYNTHETIC COMPOSITION AND METHOD FOR TREATING IRRITABLE BOWEL SYNDROME and filed on Oct. 29, 2015 for Thierry Hennet and claims priority to Denmark Application No. PC 2014 7063, which is incorporated herein by reference.

FIELD OF THE INVENTION

This invention relates generally to compositions and methods for the treatment of irritable bowel syndrome (IBS).

BACKGROUND

Description of the Related Art

Irritable bowel syndrome is a clinically heterogeneous disorder of human, particularly adult, patients with chronic symptoms such as abdominal pain, abdominal discomfort, abdominal bloating, fatigue, and changes in bowel movement patterns, such as patterns of loose or more frequent bowel movements, diarrhoea and constipation. Routine clinical tests on patients typically show no abnormalities, although their bowels may be more sensitive to certain stimuli, such as balloon insufflation testing. The worldwide prevalence of IBS is about 10-20% (Longstreth et al. *Gastroenterology* 130, 1480 (2006)) but may be higher in certain countries. The causes of IBS are unknown but disruptions of the brain-gut axis, acute gastrointestinal infections, small intestinal bacterial overgrowths, antibiotic usages and dysbiosis are thought to be important risk factors (Kim et al. *Digest. Dis. Sci.* 57, 3213 (2012)). Other risk factors are young age, prolonged fever, anxiety, and depression. Chronic low-grade inflammation commonly occurs in IBS patients, but there are otherwise little or no observable clinical manifestations.

Diagnosis of IBS is difficult. No biomarker-based tests can be performed to diagnose IBS. Diagnosis generally involves excluding conditions that produce IBS-like symptoms and then following a procedure to categorise a patient's symptoms. Ruling out parasitic infections, lactose intolerance, and celiac disease is recommended for all patients before a diagnosis of IBS is made. Once diagnosed, patients are usually classified in accordance with the Rome III criteria into four symptom subtypes based on stool consistency: diarrhoea predominant (IBS-D), constipation predominant (IBS-C), mixed subtype (IBS-M) with alternating episodes of both diarrhoea and constipation, and unsubtyped IBS (IBS-U).

There is no cure for IBS and current treatments focus on attempting to relieve symptoms. Treatments take various forms such as dietary adjustments, medication, and psychological interventions. Patient education and good doctor-patient relationships are also important. However, most treatment is unsatisfactory and most patients continue to experience chronic pain, fatigue, and other symptoms. While IBS has no direct effect on life expectancy, its high prevalence and significant effects on quality of life make it a condition with a high social cost. The general hopelessness associated with IBS is a source of frustration for both patients and health care practitioners treating them.

Current research has implicated the gastrointestinal microbiota, the brain-gut axis and the mast cells in the pathophysiology of IBS. The human gastrointestinal microbiota includes at least 1,000 species of bacteria, and about $10^{14}$ individual bacterial cells from about 160 different species inhabit each individual's intestine (Qin et al. *Nature* 464, 59 (2010)). It is believed that an individual's genetic make-up and acquired immunity, as well as environmental factors, influence their gastrointestinal microbiota. The microbiota in turn shape the individual's immunity and physiology within the gastrointestinal system. It is also believed that a healthy individual maintains a symbiotic relationship with the microbiota colonizing his/her intestines, while an individual with IBS has an imbalance in this microbiota-immune interaction.

Studies have shown that gastrointestinal microbiota of IBS patients are different from those of healthy controls. There is also evidence that gastrointestinal microbiota cause post-infectious IBS (PI-IBS). Flagellin, the primary structural component of bacterial flagella, has been shown to activate both the innate and adaptive immune system in individuals. For example, antibodies against bacteria flagellin (A4-F3a2 and Fla-X) have been detected more frequently in patients with IBS than in healthy controls ($p=0.004$ and $p=0.009$, respectively; Schoepfer et al. *Neurogastroenterol. Motil.* 20, 1110 (2008)). Also, individuals with post-infectious small intestine bacterial outgrowth (SIBO) associated with IBS may possess antibodies against flagellin proteins of the infecting bacteria (Spiller et al. *Gastroenterology* 136, 1979 (2009)). These bacteria are often *Campylobacter jejuni, Escherichia coli, Salmonella enteritidis,* and *Shigella flexneri*.

Treatments that target gastrointestinal microbiota such as antibiotics, probiotics and prebiotics appear to alleviate the symptoms of IBS; at least temporarily. For instance, the antibiotic rifaximin appears to reduce bacterial products that negatively affect the IBS patient.

Abdominal pain and discomfort associated with IBS is connected to the brain-gut axis and the response to stress hormones. IBS patients typically experience abnormal gut motility and visceral hypersensitivity mediated by the brain-gut axis or central stress response system. One arm of the brain-gut axis is the central efferent pathway, which is formed by the sympathetic nervous system and the hypothalamic-pituitary-adrenal axis (HPA). In stress-sensitive disorders including IBS, stress hormones of the HPA axis, such as adrenocorticotropic hormone (ACTH), cortisol, and catecholamine are released. Some studies have shown that the HPA axis response in IBS patients is caused by increased mucosal immune activation, which in turn increases plasma cytokine levels to stimulate the HPA axis.

In addition to the gut microbiome and the gut-brain axis, the mast cells may also play an important role in the pathogenesis of IBS. Increased mast cell infiltration and activation in distal gut segments are associated with symptom onset and severity of IBS. These cells are also implicated in the elevated response of visceral afferent nerves to mucosal stimulus in IBS patients. Mast cell hyperplasia is commonly observed following infection by the bacteria mentioned above in both post-infectious IBS and non-post-infectious IBS.

A recent development in IBS treatment has been the FODMAP diet. This diet requires patients to restrict the intake of FODMAP carbohydrates. These are Fermentable Oligo-, Di-, Monosaccharides And Polyols which are poorly absorbed in the proximal small intestine, osmotically active, and fermented by intestinal bacteria with hydrogen production. Adherence to this diet has resulted in symptom improvements for some patients (Staudacher et al. *J. Hum. Nutr. Diet.* 24, 487 (2011)). However, some of the FODMAP carbohydrates are beneficial fibres, and foods that contain them are common, highly nutritious fruits, vegetables and legumes. There has remained, however, a need for a generally safe and effective way for further improving the symptoms of IBS patients generally.

SUMMARY

In one aspect, this invention provides a synthetic composition for use in treating a patient with IBS, particularly a patient having one or more of bacterial overgrowth, dysbiosis and an impaired mucosal barrier, in reducing irritable bowel syndrome symptoms in a patient with IBS, particularly a patient having bacterial overgrowth, dysbiosis and an impaired mucosal barrier, in treating one or more chronic symptoms of abdominal pain, abdominal discomfort and/or abdominal bloating of a patient with IBS, particularly a patient having one or more of bacterial overgrowth, dysbiosis and an impaired mucosal barrier, in treating one or more chronic symptoms of changes in bowel movement patterns, such as patterns of loose or more frequent bowel movements, diarrhoea and constipation, of a patient with IBS, particularly a patient having one or more of bacterial overgrowth, dysbiosis and an impaired mucosal barrier, in preventing re-occurrence of IBS in a former patient with IBS, particularly a former patient who previously had one or more of bacterial overgrowth, dysbiosis and an impaired mucosal barrier, in increasing *Bifidobacteria,* preferably *Bifidobacterium adolescentis,* in the colon of an IBS patient for reducing IBS symptoms in the patient, particularly a patient having one or more of bacterial overgrowth, dysbiosis and an impaired mucosal barrier, and/or in preventing IBS or IBS symptoms in a patient who is undergoing or who has undergone treatment with an antibiotic, characterised in that the composition contains an effective amount of one or more human milk monosaccharides ("HMSs") or one or more human milk oligosaccharides ("HMOs"), or both. The synthetic composition is preferably a nutritional composition.

In some embodiments, the manifestation of the IBS in the patient is bacterial overgrowth and/or dysbiosis.

In another aspect, this invention provides a method for treating a patient with IBS, particularly a patient having one or more of bacterial overgrowth, dysbiosis and an impaired mucosal barrier, reducing IBS symptoms in a patient with IBS, particularly a patient having one or more of bacterial overgrowth, dysbiosis and an impaired mucosal barrier, treating one or more IBS symptoms of a patient with IBS, particularly a patient having one or more of bacterial overgrowth, dysbiosis and an impaired mucosal barrier, treating one or more chronic symptoms of changes in bowel movement patterns, such as patterns of loose or more frequent bowel movements, diarrhoea and constipation, of a patient with IBS, particularly a patient having one or more of bacterial overgrowth, dysbiosis and an impaired mucosal barrier, preventing re-occurrence of IBS in a former patient with IBS, particularly a former patient who previously had one or more of bacterial overgrowth, dysbiosis and an impaired mucosal barrier, in increasing *Bifidobacteria,* preferably *Bifidobacterium adolescentis,* in the colon of an IBS patient for reducing IBS symptoms in the patient, particularly a patient having one or more of bacterial overgrowth, and/or dysbiosis and an impaired mucosal barrier, and/or preventing IBS or IBS symptoms in a patient who is undergoing or who has undergone treatment with an antibiotic, the method comprising orally administering to the patient an effective amount of one or more HMSs or one or more HMOs, or both, preferably in the form of a synthetic composition.

In some embodiments, the manifestation of the IBS in the patient is bacterial overgrowth and/or dysbiosis.

Preferably, visceral sensitivity and defecation abnormalities are improved. For example, in IBS constipation patients, visceral sensitivity and complete spontaneous bowel movements are improved. Further, in IBS diarrhoea patients, visceral sensitivity and stool consistency are improved. The patient can be administered a higher amount, preferably 5 g to 10 g per day, of the one or more neutral HMOs for an initial treatment period, followed by a lower amount, preferably 1 g to 5 g per day, for a maintenance period. The initial treatment period can be 1 to 8 weeks. The maintenance period is at least 1 month.

In a further aspect, this invention provides a use of one or more HMSs or one or more HMOs, or both, preferably in the form of a synthetic composition, for treating/reducing IBS symptoms in a patient with IBS, particularly a patient having one or more of bacterial overgrowth, dysbiosis and an impaired mucosal barrier. In this regard, this invention provides a use of one or more HMSs or one or more HMOs, or both:

for reducing an IBS symptom in a patient with IBS, particularly a patient having one or more of bacterial overgrowth, dysbiosis and an impaired mucosal barrier, for treating one or more chronic symptoms of abdominal pain, abdominal discomfort or abdominal bloating of a patient with IBS, for treating one or more chronic symptoms of a change in bowel movement patterns, particularly a pattern of loose or more frequent bowel movements, diarrhoea or constipation, of a patient with IBS, for increasing *Bifidobacteria,* preferably *Bifidobacterium adolescentis,* in the colon of an IBS patient for reducing IBS symptoms in the patient, particularly a patient having one or more of bacterial overgrowth, and/or dysbiosis and an impaired mucosal barrier, to prevent re-occurrence of IBS in a former patient with IBS, and/or to prevent IBS or IBS symptoms in a patient who is undergoing or who has undergone treatment with an antibiotic.

In some embodiments, the manifestation of the IBS in the patient is bacterial overgrowth and/or dysbiosis.

Preferably, in all aspects of the invention, the HMS is selected from sialic acid and fucose, and the HMO is selected from 2'-FL, 3-FL, DFL, 3'-SL, 6'-SL, LNT, LNnT, LNFP-I and DSLNT. More preferably the HMO is a combination of one or more backbone HMOs and one or more fucosyl HMOs; for example 2'-FL and LNnT. 2'-FL and LNnT may be present in a mass ratio of about 4:1 to 1:1; more preferably about 3:1 to 1:1.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

These features and advantages of the present invention will become more fully apparent from the following description and appended claims, or may be learned by the practice of the invention as set forth hereinafter.

DETAILED DESCRIPTION

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

In accordance with this invention, it has been surprisingly found that human milk monosaccharides (HMSs), advantageously sialic acid and/or fucose, and human milk oligosaccharides (HMOs), advantageously 2'-FL, 3-FL, LNT, LNnT, 3'-SL, 6'-SL, DFL, DSLNT and/or LNFP-I, are able to reduce chronic symptoms of irritable bowel syndrome in IBS patients, particularly those who are suffering from bacterial overgrowth, dysbiosis or an impaired mucosal barrier. Further, it has been found that HMSs/HMOs reduce the risk of re-occurrence of IBS in patients, particularly those who are suffering from bacterial overgrowth, dysbiosis or an impaired mucosal barrier. It is believed that the HMSs/HMOs can: (1) act as prebiotics to promote beneficial bacteria growth and reduce bacterial overgrowth and dysbiosis; (2) act as decoys for pathogens by binding to them and thereby reduce/prevent binding of the pathogens to epithelial cells in the gastrointestinal tract; (3) act to reduce chronic mucosal inflammation; and/or (4) repair damage to the mucosal barrier. The HMSs/HMOs can also act on neuronally dependent gut migrating motor complexes to address disorders of gut motility and possibly have beneficial effects on the central nervous systems of patients.

The term "oral administration" preferably means any conventional form for the oral delivery of a composition to a patient that causes the deposition of the composition in the gastrointestinal tract (including the stomach) of the patient. Accordingly, oral administration includes swallowing of composition by the patient, enteral feeding through a nasogastric tube, and the like.

The term "effective amount" preferably means an amount of a composition that provides a human milk monosaccharide or human milk oligosaccharide in a sufficient amount to render a desired treatment outcome in a patient. An effective amount can be administered in one or more doses to the patient to achieve the desired treatment outcome.

The term "human milk monosaccharide" or "HMS" preferably means a monosaccharide found in human breast milk. Examples include sialic acid and L-fucose. In human milk, the sialic acid is N-acetylneuraminic acid.

The term "human milk oligosaccharide" or "HMO" preferably means a complex carbohydrate found in human breast milk that can be in acidic or neutral form. More than about 200 different HMO structures are known to exist in human breast milk (Urashima et al.: Milk Oligosaccharides, Nova Biomedical Books, New York, 2011). HMOs can be backbone, fucosylated and sialylated oligosaccharides. Backbone HMOs consists of Glu, Gal and GlcNAc and are devoid of Fuc and sialic acid. Examples of backbone HMOs include lacto-N-tetraose (LNT), lacto-N-neotetraose (LNnT), lacto-N-neohexaose (LNnH) and lacto-N-hexaose (LNH). Fucosyl HMOs are fucosylated lactoses or fucosylated backbone HMOs such as 2'-fucosyllactose (2'-FL), lacto-N-fucopentaose I (LNFP-I), lacto-N-difucohexaose I (LNDFH-I), 3-fucosyllactose (3-FL), difucosyllactose (DFL), lacto-N-fucopentaose III (LNFP-III), fucosyl-para-lacto-N-neohexaose (F-pLNnH), lacto-N-difucohexaose I (LNDFH-I), fucosyl-lacto-N-hexaose II (FLNH-II), lacto-N-fucopentaose V (LNFP-V), lacto-N-difucohexaose II (LNDFH-II), fucosyl-lacto-N-hexaose I (FLNH-I), fucosyl-lacto-N-hexaose III (FLNH-III) and fucosyl-para-lacto-N-neohexaose (F-pLNnH). Sialyl HMOs are sialylated lactoses or sialylated backbone HMOs such as 3',6-disialyllacto-N-tetraose (DSLNT), 6'-sialyllactose (6'-SL), 3'-sialyllactose (3'-SL), 6'-sialyllacto-N-neotetraose (LST c), 3'-sialyllacto-N-tetraose (LST a) and 6-sialyllacto-N-tetraose (LST b). HMOs containing both sialyl and fucosyl groups may be considered to belong to either of the latter two groups. Examples for sialyl and fucosyl HMOs include disialyl-fucosyl-lacto-N-hexaose II (DSFLNH-II), fucosyl-sialyl-lacto-N-neohexaose I (FSLNnH-I), fucosyl-sialyl-lacto-N-hexaose I (FSLNH-I) and 3-fucosyl-3'-sialyllactose (FSL).

The terms "microbiota", "microflora" and "microbiome" preferably mean a community of living microorganisms that typically inhabits a bodily organ or part. The most dominant members of the gastrointestinal microbiota include microorganisms of the phyla of *Firmicutes, Bacteroidetes, Actinobacteria, Proteobacteria, Synergistetes, Verrucomicrobia, Fusobacteria,* and *Euryarchaeota;* at genus level the microorganisms of *Bacteroides, Faecalibacterium, Bifidobacterium, Roseburia, Alistipes, Collinsella, Blautia, Coprococcus, Ruminococcus, Eubacterium* and *Dorea;* and at species level microorganisms of *Bacteroides uniformis, Alistipes putredinis, Parabacteroides merdae, Ruminococcus bromii, Dorea longicatena, Bacteroides caccae, Bacteroides thetaiotaomicron, Eubacterium hallii, Ruminococcus torques, Faecalibacterium prausnitzii, Ruminococcus lactaris, Collinsella aerofaciens, Dorea formicigenerans,*

*Bacteroides vulgatus* and *Roseburia intestinalis*. In some instances, the gastrointestinal microbiota includes the mucosa-associated microbiota, which is located in or attached to the mucus layer covering the epithelium of the gastrointestinal tract, and luminal-associated microbiota, which is found in the lumen of the gastrointestinal tract.

The terms "irritable bowel syndrome" and "IBS" preferably mean a group of functional bowel disorders of humans, particularly adults, characterized by one or more chronic symptoms including abdominal pain, abdominal discomfort, abdominal bloating, fatigue, and changes in bowel movement patterns, such as patterns of loose or more frequent bowel movements, diarrhoea and constipation, typically in the absence of any apparent structural abnormality. There are at least three forms of IBS, depending on which symptom predominates: (1) diarrhoea-predominant (IBS-D); (2) constipation-predominant (IBS-C); and (3) IBS with alternating stool pattern (IBS-A or IBS-M). There are also various clinical subtypes of IBS, such as post-infectious IBS (IBS-PI).

The HMOs can be isolated or enriched by well-known processes from milk(s) secreted by mammals including, but not limited to human, bovine, ovine, porcine, or caprine species. The HMOs can also be produced by well-known processes using microbial fermentation, enzymatic processes, chemical synthesis, or combinations of these technologies. As examples, using chemistry LNnT can be made as described in WO 2011/100980 and WO 2013/044928, LNT can be synthesized as described in WO 2012/155916 and WO 2013/044928, a mixture of LNT and LNnT can be made as described in WO 2013/091660, 2'-FL can be made as described in WO 2010/115934 and WO 2010/115935, 3-FL can be made as described in WO 2013/139344, 6'-SL and salts thereof can be made as described in WO 2010/100979, sialylated oligosaccharides can be made as described in WO 2012/113404 and mixtures of human milk oligosaccharides can be made as described in WO 2012/113405. As examples of enzymatic production, sialylated oligosaccharides can be made as described in WO 2012/007588, fucosylated oligosaccharides can be made as described in WO 2012/127410, and advantageously diversified blends of human milk oligosaccharides can be made as described in WO 2012/156897 and WO 2012/156898. With regard to biotechnological methods, WO 01/04341 and WO 2007/101862 describe how to make core human milk oligosaccharides optionally substituted by fucose or sialic acid using genetically modified *E. coli*.

A synthetic composition of this invention comprising one or more human milk monosaccharides or one or more human milk oligosaccharides, or both can take any suitable form. For example, the composition can be in the form of a nutritional composition which contains other macronutrients such as proteins, lipids or other carbohydrates. The synthetic composition can also be a pharmaceutical composition. In one embodiment, the synthetic compositions contains one or more backbone HMOs and one or more fucosyl HMOs and optionally fucose. In another embodiment, the synthetic composition contains one or more backbone HMOs and one or more sialyl HMOs and optionally sialic acid. In a further embodiment, the synthetic composition comprises one or more fucosyl HMOs and one or more sialyl HMOs, and optionally fucose and/or sialic acid, preferably both. In a preferred embodiment, the synthetic composition contains one or more backbone HMOs, one or more sialyl HMOs and one or more fucosyl HMOs, and optionally fucose and/or sialic acid, preferably both.

Nutritional Compositions

A nutritional composition of this invention can contain sources of protein, lipids and/or digestible carbohydrates and can be in powdered or liquid forms. The composition can be designed to be the sole source of nutrition or a nutritional supplement. For IBS patients, a nutritional supplement is preferred; especially a supplement which can form a meal or snack replacement. Preferably the nutritional composition is lactose-reduced or, better yet, lactose-free. Preferably, the nutritional composition is also free from, or low in amounts of, FODMAP carbohydrates.

Suitable protein sources include milk proteins, soy protein, rice protein, pea protein and oat protein, or mixtures thereof. Milk proteins can be in the form of milk protein concentrates, whey protein or casein, or mixtures of both. Soy, rice, pea and oat protein can be in the form or protein isolated. The protein can be whole protein or hydrolysed protein, either partially hydrolysed or extensively hydrolysed. The protein can provide about 5% to about 50%, preferably about 10% to 30%, of the energy of the nutritional composition. The protein source preferably is not a source of non-fermentable carbohydrates such as lactose. Therefore, if a milk protein is used as the protein source, the milk protein is preferably lactose-reduced or lactose-free.

Suitable digestible carbohydrates include maltodextrin, hydrolysed or modified starch or corn starch, glucose polymers, corn syrup, corn syrup solids, tapioca, sucrose, and glucose, or mixtures thereof. Generally digestible carbohydrates provide about 35% to about 75%, preferably about 45% to 70%, of the energy of the nutritional composition. Preferably the digestible carbohydrate is free from lactose.

Suitable lipids include rapeseed oil, sunflower seed oil, palm oil, soy oil, milk fat, corn oil and soy lecithin. Long-chain poly unsaturated fatty acids (LC-PUFA), especially omega-3 fatty acids such as docosahexaenoic acid (DHA), can be included in the lipid source because they have anti-inflammatory properties. Suitable sources of LC-PUFA are plant oils, marine plankton oils, fungal oils, and fish oils. The lipid source can also include medium chain triglycerides (MCT). Fractionated coconut oils are a suitable source of medium chain triglycerides. The lipid source preferably provides about 5% to about 25% of the energy of the nutritional composition; for example about 10% to 20%. The lipid content is preferably reduced because high fat diets can provoke IBS symptoms.

The nutritional composition preferably also includes vitamins and minerals. If the nutritional composition is intended to be a sole source of nutrition, it preferably includes a complete vitamin and mineral profile. Examples of vitamins include Vitamins A, B-complex (such as B1, B2, B6 and B12), C, D, E and K, niacin and acid vitamins such as pantothenic acid and folic acid and biotin. Examples of minerals include calcium, iron, zinc, magnesium, iodine, copper, phosphorus, manganese, potassium, chromium, molybdenum, selenium, nickel, tin, silicon, vanadium and boron.

The nutritional composition can also include a carotenoid such as lutein, lycopene, zeaxanthin, and beta-carotene. The total amount of carotenoid included can vary from about 0.001 µg/ml to about 10 µg/ml. Lutein can be included in an amount of from about 0.001 µg/ml to about 10 µg/ml, preferably from about 0.044 µg/ml to about 5 g/ml of lutein. Lycopene can be included in an amount from about 0.001 µg/ml to about 10 µg/ml, preferably about 0.0185 mg/ml to about 5 g/ml of lycopene. Beta-carotene can comprise from about 0.001 µg/ml to about 10 mg/ml, for example about 0.034 µg/ml to about 5 µg/ml of beta-carotene.

The nutritional composition can also contain various other conventional ingredients such as preservatives, emulsifying agents, thickening agents, buffers, fibres and probiotics, especially probiotics which can help to reduce symptoms in IBS patients (e.g. VSL#3, B. infantis 35624, B. animalis subsp. lactis BB-12, B. lactis Bi-07, L. rhamnosus GG, L. rhamnosus Lc705, L. plantarum DSM 9843, L. plantarum CECT7484, L. plantarum CECT7485, L. acidophilus NCFM, L. fermentum CECT5716, B. breve Bb99, Propionibacterium freundenreichii ssp. Shermanii JS, P. acidilactici CECET7483, Streptococcus faecium), antioxidant/anti-inflammatory compounds including tocopherols, carotenoids, ascorbate/vitamin C, ascorbyl palmitate, polyphenols, glutathione, and superoxide dismutase (melon), other bioactive factors (e.g. growth hormones, cytokines, TFG-β), colorants, flavours, and stabilisers, lubricants, and so forth.

The nutritional composition can be in the form of a soluble powder, a liquid concentrate, or a ready-to-use formulation. Various flavours, fibres and other additives can also be present.

The nutritional compositions can be prepared by any commonly used manufacturing techniques for preparing nutritional compositions in solid or liquid form. For example, the composition can be prepared from various feed solutions. A protein-in-fat feed solution can be prepared by heating and mixing the lipid source and then adding an emulsifier (e.g., lecithin), fat soluble vitamins, and at least a portion of the protein source while heating and stirring. A carbohydrate feed solution is also prepared by adding minerals, trace and ultra trace minerals, thickening or suspending agents to water while heating and stirring. The resulting solution is held for 10 minutes with continued heat and agitation before adding carbohydrates (e.g., the HMOs and digestible carbohydrate sources). The resulting feed solutions are then blended together while heating and agitating and the pH adjusted to 6.6-7.0, after which the composition is subjected to high-temperature short-time processing during which the composition is heat treated, emulsified and homogenized, and then allowed to cool. Water soluble vitamins and ascorbic acid are added, the pH is adjusted to the desired range if necessary, flavours are added, and water is added to achieve the desired total solid level.

For a liquid product, the resulting solution can then be aseptically packaged to form an aseptically packaged nutritional composition. In this form, the nutritional composition can be in ready-to-feed or concentrated liquid form. Alternatively the composition can be spray dried and processed and packaged as a reconstitutable powder.

When the nutritional product is a ready-to-feed nutritional liquid, the total concentration of HMS/HMOs in the liquid, by weight of the liquid, is from about 0.0001% to about 2.0%, including from about 0.001% to about 1.5% and from about 0.01% to about 1.0%; or from about 0.002% to about 3.0%, including from about 0.005% to about 2% and from about 0.05% to about 1.0%. When the nutritional product is a concentrated nutritional liquid, the total concentration of HMS/HMOs in the liquid, by weight of the liquid, is from about 0.0002% to about 4.0%, including from about 0.002% to about 3.0% and from about 0.02% to about 2.0%; or from about 0.004% to about 6.0%, including from about 0.01% to about 4.0% and from about 0.1% to about 2.0%.

Unit Dosage Forms

The synthetic composition of this invention can also be in a unit dosage form such as a capsule, tablet or sachet. For example, the composition can be in a tablet form comprising the human milk monosaccharides and/or oligosaccharides, and one or more additional components to aid formulation and administration, such as diluents, excipients, antioxidants, lubricants, colorants, binders, disintegrants, and the like.

Suitable diluents, excipients, lubricants, colorants, binders, and disintegrants include polyethylene, polyvinyl chloride, ethyl cellulose, acrylate polymers and their copolymers, hydroxyethyl-cellulose, hydroxypropylmethyl-cellulose (HPMC), sodium carboxymethylcellulose, polyhydroxyethyl methacrylate (PHEMA), polyvinyl alcohol (PVA), polyvinyl pyrrolidone (PVP), polyethylene oxide (PEO), or polyacrylamide (PA), carrageenan, sodium alginate, polycarbophil, polyacrylic acid, tragacanth, methyl cellulose, pectin, natural gums, xanthan gum, guar gum, karaya gum, hypromellose, magnesium stearate, microcrystalline cellulose, and colloidal silicon dioxide. Suitable antioxidants are vitamin A, carotenoids, vitamin C, vitamin E, selenium, flavonoids, polyphenols, lycopene, lutein, lignan, coenzyme Q10 ("CoQIO") and glutathione.

The unit dosage forms, especially those in sachet form, can also include various nutrients including macronutrients.

Administration Dosing

For reducing IBS symptoms in a patient having bacterial overgrowth, dysbiosis and/or an impaired mucosal barrier, the amount of HMS(s) and/or HMO(s) required to be administered to the patient will vary depending upon factors such as the risk and severity of the disease, the age of the patient, the form of the composition, and other medications being administered to the patient. However, the required amount can be readily determined by a medical practitioner and would generally be in the range of about 20 mg to about 20 g per day, in certain embodiments preferably about 50 mg to about 10 g per day, more preferably from about 100 mg to about 7.5 g per day, even more preferably from about 500 mg to about 5 g per day, especially from about 1 g to about 2.5 g per day; in other embodiments preferably about 50 mg to about 20 g per day, more preferably from about 100 mg to about 15 g per day, even more preferably from about 500 mg to about 10 g per day, especially from about 1 g to about 7.5 g per day. During an initial treatment phase, the dosing can be higher; for example 100 mg to 20 g or 100 mg to 30 g per day, preferably 500 mg to 15 g per day, more preferably 1 g to 10 g per day, in certain embodiments 2.5 g to 7.5 g per day. During a secondary prevention phase, the dosing can be reduced; for example, in certain embodiments, to 20 mg to 10 g per day, preferably to 100 mg to 7.5 g per day, more preferably to 500 mg to 2.5 g per day, even more preferably to 750 mg to 1.5 g per day, or, in other embodiments, to 20 mg to 20 g per day, preferably to 100 mg to 10 g per day, more preferably to 500 mg to 7.5 g per day, even more preferably to 750 mg to 5 g per day.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

EXAMPLES

Examples are now described to further illustrate the invention:

Example 1

Human Trial

A total of 60 male and female IBS patients are recruited to participate in the study. After a screening visit and run-in period of 1-2 weeks, the patients are selected. The patients are randomized into three groups, each of 20 patients, with two groups consuming the treatment product and one group the placebo product for 8 weeks. The treatment product contains either 5 or 10 grams of a combination of 2'-FL, LNnT, LNT, 3-FL, 6'-SL and 3'-SL while the control product contains 2 grams glucose. Both products are in powder form in a unit dosage container.

The patients are eligible to participate if they are at least 18 years of age, meet the Rome III criteria for IBS, and are diagnosed with bacterial overgrowth/dysbiosis. All recruited patients are able and willing to understand and comply with the study procedures. Patients are excluded if: they have participated in a clinical study one month prior to screening visit; they have abnormal results in the screening tests which are clinically relevant for study participation; they are suffering for a severe disease such as malignancy, diabetes, severe coronary disease, kidney disease, neurological disease, or severe psychiatric disease or any condition which can confound the results of the study; used highly dosed probiotic supplements (yoghurt allowed) for 3 months prior to the study; consumed antibiotic drugs 3 months prior to the study; consumed on a regular basis any medication that might interfere with symptom evaluation 2 weeks prior to the study; and pregnant or lactating.

At the screening visit, medical history and concomitant medication is registered and a blood sample for safety analyses is collected. A faecal sample kit is distributed. Patients are instructed to keep their samples in the freezer until the next visit.

At the second visit, eligibility criteria are checked and eligible subjects are randomised to the three arms in the trial. The faecal samples are collected and equipment for new samples are distributed. Patients are familiarised with an interactive internet enabled system which records data daily and are provided with either treatment or control products. Subjects are reminded not to change their usual diet during the study. Blood samples are collected for biomarker studies.

The serum from the blood samples is transferred to cryotubes and stored at −80° C. The following biomarkers are measured Aldosteron, Angiotensin II, ApoAl, ApoB, Blood urea nitrogen, Iron, BNP (Brain natriuretic peptide), Cortisol, ECP (Eosinophilic cationic protein), Estradiol, FFA (Aliphatic carboxylate), Glucagon, HbAlc, IgA, IgM, IgG, IL-10, IL-6, Insulin, Lysozyme, Progesteron, Testosterone, TNF-α, Transferrin, Vitamin A, Vitamin B1, Vitamin B12, Vitamin B6, Vitamin D, Vitamin K1, A-1-antitrypsin.

The faecal samples are stored at −80° C. until analysis. Faecal samples are subjected to 16 S RNA sequencing analysis.

The study runs for 8 weeks with the patients consuming either a placebo or a treatment product daily. Patients are instructed to consume the products in the morning with breakfast. Compliance is monitored through the interactive internet enabled system. The patients also use the system to record:
Bristol Stool Form Scale (BSF) information,
Symptom information such as abdominal pain, abdominal discomfort, abdominal cramping, abdominal bloating, and abdominal fullness,
Additional Gastrointestinal Symptom Rating Scale (GSRS) information.

This questionnaire includes 15 items covering five dimensions (abdominal pain, indigestion, reflux, diarrhoea, constipation) and uses a seven-graded Likert scale.

At the end of the study, each patient has an exit visit with the medical team. Faecal samples and blood samples are collected and analysed as before.

The treatment patients report a reduction in pain and an improvement in bowel movement as compared to the placebo group. The blood biomarker analysis indicates that the treatment patients have reduced levels of inflammatory markers. The faecal analysis indicates that the treatment patients have reduced levels of bacterial overgrowth/dysbiosis.

Example 2

Human Trial

A total of 300 male and female IBS patients are recruited to participate in the study. After a screening visit and run-in period of 1-2 weeks, the patients are selected. The patients are randomized into two groups, each of 150 patients, with one group consuming the treatment product and one group the placebo product for 8 weeks. The treatment product contains 5 grams of a combination of 2'-FL and LNnT while the control product contains 2 grams glucose. Both products are in powder form in a unit dosage container.

The patients are eligible to participate if: they are between 18 and 60 years of age; meet the Rome III criteria for IBS; report a weekly average of worst daily abdominal pain intensity score of ≥3 on a 0-10 point scale; report a pain/discomfort frequency of at least 2 days a week during screening evaluation; report fewer than three complete spontaneous bowel movements (CSBMs) per week for IBS-C subgroup of patients; and at least one stool with a consistency of Type 6 or Type 7 Bristol stool (BSS) on at least 2 days per week for IBS-D subgroup of patients. All recruited patients are able and willing to understand and comply with the study procedures. Patients are excluded if: they have participated in a clinical study one month prior to screening visit; they have abnormal results in the screening tests which are clinically relevant for study participation; they are suffering for a severe disease such as malignancy, diabetes, severe coronary disease, kidney disease, neurological disease, or severe psychiatric disease or any condition which can confound the results of the study; used highly dosed probiotic supplements (yoghurt allowed) for 3 months prior to the study; consumed antibiotic drugs 3 months prior to the study; consumed on a regular basis any medication that might interfere with symptom evaluation 2 weeks prior to the study; and pregnant or lactating.

At the initial visit (screening), each patient is given both written and oral information about the study and the patient is asked to sign an informed consent form.

Patients are evaluated by a full review of clinical history, and based on clinical symptoms, characterised into one of the three following groups; diarrhoea predominant (IBS-D), constipation predominant (IBS-C) or alternating/mixed (IBS-A/M). This enables allocation of patients into subgroups at post-analysis.

A blood sample for eligibility analysis is collected. A talk through of the electronic questionnaires (GSRS, IBS-SSS, QoL and BSFS) is performed to familiarise the patients with the electronic system, and equipment for faecal sampling is distributed to each patient. Patients are instructed to keep their samples in the freezer until the next visit.

At the second visit (beginning of intervention), eligibility criteria are checked and eligible subjects are randomised to the two arms in the trial. Symptoms (as measured by GSRS, IBS-SSS, BSFS and QoL scales) are assessed. Trial supplementation is distributed along with instructions on use of an electronic compliance diary. The faecal samples are collected and equipment for collecting new samples are distributed. Patients are reminded not to change their usual diet during the study.

Blood samples are collected for biomarker studies and biobanking. The serum from the blood samples is transferred to cryotubes and stored at −80° C. The following biomarkers are measured TNF-α, IL-10, IL-8, IL-6, IL-12, IL-10, MIP-1β, hs-CRP, lipopolysaccharide binding protein, tryptase, antiflagellin, zonulin, histamine, prostaglandin 2, and cortisol.

The faecal samples are stored at −80° C. until analysis. Microbiological analysis is performed on the faecal samples using the 16S rRNA gene sequence.

The study runs for 8 weeks with the patients consuming either a placebo or a treatment product daily. Patients are instructed to consume the products in the morning with breakfast. Compliance is monitored through the interactive internet enabled system. The patients also use the system to record:

Bristol Stool Form Scale (BSFS) information,
Symptom information such as abdominal pain, abdominal discomfort, abdominal cramping, abdominal bloating, and abdominal fullness,
Quality of life (QoL) information,
IBS severity scoring system (IBS-SSS) information,
Additional Gastrointestinal Symptom Rating Scale (GSRS) information. This questionnaire includes 15 items covering five dimensions (abdominal pain, indigestion, reflux, diarrhoea, constipation) and uses a seven-graded Likert scale.

4 weeks after commencement, there is an intermediate check. A physical examination is done and symptoms (as measured by GSRS, IBS-SSS, BSFS and QoL scales etc.) are reassessed. Faecal samples and blood samples are collected and analysed as before, and equipment for collection of new faecal samples are distributed.

At the end of the intervention (8 weeks), each patient has a visit with the medical team. A physical examination is done and symptoms (as measured by GSRS, IBS-SSS, BSFS and QoL scales etc.) are reassessed. Trial supplementation products are collected to check compliance. Faecal samples and blood samples are collected and analysed as before.

At this visit, the participants are asked if they wish to continue in an open label follow up study. Fifty percent of the participants continuing are given half the dose of the active product and the rest are not taking the product. The patients agreeing to continue are given equipment for faecal sample collection and for the patients continuing on active product, trial supplementation is distributed.

At the end of the study, the patients have a final visit where faecal samples are collected and symptoms (as measured by GSRS, IBS-SSS, BSFS and QoL scales) are reassessed from the patients of the open label follow-up study. Additionally, they are asked about any adverse events.

For patients not participating in the open label follow up study, this visit will only be relevant, if they have adverse events. This visit may be completed via telephone. The treatment patients report a reduction in pain/visceral sensitivity and an improvement in bowel movement as compared to the placebo group. The blood biomarker analysis indicates that the treatment patients have reduced levels of inflammatory markers, reduced gut permeability indicating an improved mucosal barrier, and reduced evidence of mast cell degranulation. The faecal analysis indicates that the treatment patients have reduced levels of bacterial overgrowth/dysbiosis and a higher level of *Bifidobacteria*; especially *Bifidobacterium adolescentis*.

Example 3

Nutritional Composition

A ready to feed nutritional composition is prepared from water, maltodextrin, corn syrup, sugar, milk protein concentrate, vegetable oil (canola, high oleic sunflower and corn), soy protein isolate, acacia gum, flavours, HMOs, potassium citrate, magnesium phosphate, cellulose gel and gum, calcium carbonate, sodium ascorbate, soy lecithin, choline bitartrate, calcium phosphate, alpha-tocopheryl acetate, ascorbic acid, carrageenan gum, ferric pyrophosphate, flavours, sweeteners (Stevia), vitamin A palmitate, niacinamide, vitamin D3, calcium pantothenate, manganese sulphate, copper sulphate, pyridoxine hydrochloride, thiamine hydrochloride, beta carotene, riboflavin, chromium chloride, folic acid, biotin, potassium iodide, phytonadione, sodium selenite, sodium molybdate, vitamin B12.

The composition provides a nutritional supplement which is a good source of protein, low in fat, vitamins, minerals and antioxidants, and meets FODMAP criteria. Further, the composition contains HMO's which are able to promote the growth of beneficial intestinal bacteria and modulate chronic inflammation.

Example 4

Capsule Composition

A capsule is prepared by filling about 1 g of HMS/HMO into a 000 gelatine capsule using a filing machine. The capsules are then closed. The HMS/HMO are in free flowing, powder form.

Example 5

Mucosal Barrier Function

2'-FL and LNnT are tested with respect to their ability to induce MUC2, TFF3, EIMβ, CHST5, and GAL3ST2 expression in the human LS174T cell culture model of goblet cells. The human LS174T cell line is obtained from the American Type Culture Collection (ATCC). LS174T cells are maintained in minimum essential medium (MEM) supplemented according to instructions at 37° C. in 5% $CO_2$. 2'-FL and LNnT are dissolved in cell culture grade water to the required concentration. The LS174T cells are treated with the HMO solution containing 0 or 5 mg HMO/ml.

The LS174T cells are collected and suspended in Trizol reagent and total RNA is isolated using an RNA analysis kit (Qiagen) according to the manufacturer's instructions and the RNA isolates are quantified using Nanodrop analysis (Thermo Fisher Scientific). RNA isolates are reverse transcribed using a high capacity cDNA Reverse Transcription Kit (Applied Biosystems) to create cDNA, which is then used to assess gene expression via quantitative RT-PCR.

For the quantitative RT-PCR, specific TaqMAN gene expression assays are obtained from Applied Biosystems, which include expression assays for MUC2, TFF3, CHST5 and GAL3ST2. Quantitative real-time PCR is performed using TaqMAN PCR Master Mix (Applied Biosystems). Reactions are run in duplicates in a 384-well plate using an Applied Biosystems 7900HT Fast Real-Time PCR System. The results are analysed using SDS 2.3 software and calculated by delta delta Ct method. All samples are normalized to Gus-β expression and fold induction is calculated over untreated controls. Gene expression is expressed as fold increase compared to HMO-free control cells. The experiment is repeated three times.

The results indicate that treatment with 2'-FL and LNnT increases the expression of the MUC2 and TFF3 genes compared to control cultures. Increased expression of goblet cell genes is specific and not universal, as evidenced by the minimal induction or lack of induction of CHST5 and GAL3 ST2, respectively. MUC2 and TFF3 are key components of the mucosal barrier and improve mucosal barrier function.

What is claimed is:

1. A method comprising:
   selecting an adult human patient with irritable bowel syndrome (IBS) experiencing one or more IBS symptoms;
   selecting an amount of a mixture of 2'-fucosyllactose (2'-FL) and lacto-N-neotetraose (LNnT) effective for increasing a relative abundance of *Bifidobacterium adolescentis* in the gastrointestinal microbiota of the adult human patient; and
   increasing the relative abundance of *Bifidobacterium adolescentis* in the gastrointestinal microbiota of the adult human patient and reducing the likelihood of the adult human patient experiencing the one or more IBS symptoms by administering a daily dose of the selected effective amount of the mixture of 2'-FL and LNnT to the adult human patient.

2. The method of claim 1, wherein the adult human patient has undergone treatment with an antibiotic to reduce bacteria that negatively affect the IBS, and wherein the adult human patient has not consumed the antibiotic in a three-month period prior to the administering of the selected effective amount of the mixture of 2'-FL and LNnT.

3. The method of claim 1, wherein the one or more IBS symptoms are chronic symptoms selected from abdominal pain, abdominal discomfort, abdominal bloating, change in bowel movement patterns, diarrhea, and constipation.

4. The method of claim 1, wherein the daily dose of the mixture of the selected effective amount of the 2'-FL and LNnT administered to the adult human patient is from about 2.5 g to about 20 g.

5. The method of claim 4, further comprising administering with the selected effective amount of the mixture of 2'-FL and LNnT, one or more sialylated human milk oligosaccharides (HMOs) selected from 6'-sialyllactose (6'-SL) and 3'-sialyllactose (3'-SL)'.

6. The method of claim 1, further comprising administering with the selected effective amount of the mixture of 2'-FL and LNnT, one or more neutral HMOs selected from 3-fucosyllactose (3-FL), lacto-N-fucopentaose I (LNFP-I), and difucosyllactose (DFL).

7. The method of claim 1, wherein a mass ratio of the 2'-FL to the LNnT in the administered selected effective amount of the mixture is from about 4:1 to 1:1.

8. The method of claim 1, wherein the selected effective amount of the mixture of the 2'-FL and LNnT is administered for a treatment period of from 1 week to 8 weeks.

9. The method of claim 1, wherein the adult human patient is administered a daily dose of from 5 g to 10 g of the selected effective amount of the mixture of the 2'-FL and LNnT for an initial treatment period of from 1 week to 8 weeks, followed by a daily dose of from 1 g to 5 g of the selected effective amount of the mixture of the 2'-FL and LNnT for a maintenance period of at least 1 month.

10. A method comprising:
    selecting a non-infant human patient who has been previously treated for one or more symptoms associated with irritable bowel syndrome (IBS);
    selecting an amount of a mixture of 2'-fucosyllactose (2'-FL) and lacto-N-neotetraose (LNnT) effective for increasing a relative abundance of *Bifidobacterium adolescentis* in the gastrointestinal microbiota of the non-infant human patient; and
    increasing the relative abundance of *Bifidobacterium adolescentis* in the gastrointestinal microbiota of the non-infant human patient and reducing in the non-infant human patient a risk of re-occurrence of one or more symptoms associated with IBS by administering a daily dose of the selected effective amount of the mixture of 2'-FL and LNnT and optionally one or more excipients, to the non-infant human patient, wherein the daily dose of the mixture is from about 2.5 g to about 20 g.

11. The method of claim 10, wherein the non-infant human patient has undergone treatment with an antibiotic and wherein the non-infant human patient has not consumed the antibiotic in a three-month period prior to the administering of the selected effective amount of the mixture of 2'-FL and LNnT.

12. The method of claim 10, further comprising reducing the severity in the non-infant human patient of one or more chronic symptoms selected from the following group: abdominal pain, abdominal discomfort, abdominal bloating, changes in bowel movement patterns, diarrhea, and constipation, by administering the selected effective amount of the mixture of 2'-FL and LNnT to the non-infant human patient.

13. The method of claim 10, further comprising reducing the re-occurrence in the non-infant human patient of one or more chronic symptoms selected from abdominal pain, abdominal discomfort, abdominal bloating, change in bowel movement patterns, diarrhea, and constipation, by administering the selected effective amount of the mixture of 2'-FL and LNnT to the non-infant human patient.

14. The method of claim 13, further comprising administering with the selected effective amount of the mixture of 2'-FL and LNnT, one or more sialylated HMOs selected from 6'-sialyllactose (6'-SL) and 3'-sialyllactose (3'-SL).

15. The method of claim 10, further comprising administering with the selected effective amount of the mixture of 2'-FL and LNnT, one or more neutral HMOs selected from 3-fucosyllactose (3-FL), lacto-N-fucopentaose I (LNFP-I), and difucosyllactose (DFL).

16. The method of claim 10, wherein a mass ratio of the 2'-FL to the LNnT in the administered selected effective amount of the mixture is from about 4:1 to 1:1.

17. The method of claim 10, wherein the selected effective amount of the mixture of the 2'-FL and LNnT is administered for a treatment period of from 1 week to 8 weeks.

18. The method of claim 10, wherein the non-infant human patient is administered a daily dose of from 5 g to 10 g of the selected effective amount of the mixture of the 2'FL and LNnT for an initial treatment period of from 1 week to 8 weeks, followed by a daily dose of from 1 g to 5 g of the selected effective amount of the mixture of the 2'FL and LNnT for a maintenance period of at least 1 month.

19. A method comprising:
   selecting a non-infant human patient experiencing one or more symptoms associated with irritable bowel syndrome (IBS);
   selecting an amount of a mixture of 2'-fucosyllactose (2'-FL) and lacto-N-neotetraose (LNnT) effective for increasing a relative abundance of *Bifidobacterium adolescentis* in the gastrointestinal microbiota of the non-infant human patient; and
   increasing the relative abundance of *Bifidobacterium adolescentis* in the gastrointestinal microbiota of the non-infant human patient and reducing in the non-infant human patient the level of one or more inflammatory biomarkers or symptoms associated with the IBS by administering a daily dose of the selective effective amount of the mixture of 2'FL and LNnT to the non-infant human patient.

20. The method of claim 19, wherein the one or more inflammatory biomarkers associated with the IBS are selected from tumor necrosis factor alpha (TNFα), interleukin 6 (IL-6), high-sensitivity C-reactive protein (hs-CRP), and lipopolysaccharide binding protein (LBP).

* * * * *